United States Patent [19]

Beemsterboer et al.

[11] 4,145,345

[45] Mar. 20, 1979

[54] CHROMATOGRAPHIC PURIFICATION OF MAYTANSINE

[75] Inventors: George L. Beemsterboer, Dayton; Joseph Satanek, Jr., Xenia, both of Ohio

[73] Assignee: Research Corporation, New York, N.Y.

[21] Appl. No.: 858,450

[22] Filed: Dec. 7, 1977

[51] Int. Cl.² .......................................... C07D 413/14
[52] U.S. Cl. ............................................. 260/239.3 T
[58] Field of Search ................................. 260/239.3 T

[56] References Cited

U.S. PATENT DOCUMENTS 3,896,111  7/1975  Kupchan et al. ............. 260/239.3 T

FOREIGN PATENT DOCUMENTS 2241418  3/1972  Fed. Rep. of Germany .... 260/239.3 T

*Primary Examiner*—Natalie Trousof
*Assistant Examiner*—Robert T. Bond
*Attorney, Agent, or Firm*—Omri M. Behr

[57] ABSTRACT

There is provided a high yield mode of separating maytansine from other maytansinoid components associated therewith in extracts thereof from natural sources. The procedure comprises two sequential chromatographic steps on silica gel in different solvent systems.

7 Claims, No Drawings

CHROMATOGRAPHIC PURIFICATION OF MAYTANSINE

BACKGROUND OF THE INVENTION

In U.S. Pat. No. 3,896,111 of July 22, 1975, to Kupchan et al., it is disclosed that certain African woods, in particular *Maytenus buchananii* and *Maytenus ovatus*, contain certain factors which demonstrate significant anti-leukemic activity in the microgram/kilogram level. One of these factors, which structure is disclosed in the patent, is designated as maytansine.

The patent to Kupchan et al. discloses a number of extraction steps leading to the provision of an active concentrate. This concentrate is provided by the sequential steps of extraction of the wood chips with 95% aqueous ethanol, partition of said extract between water and ethyl acetate, treatment of said ethyl acetate extract first with aqueous sodium hydroxide and subsequently with aqueous hydrochloric acid. The thus treated extract is then acylated in order to solubilize certain impurities. The acylated mixture is partitioned between aqueous methanol and carbon tetrachloride, and the methanol fraction further partitioned with chloroform. The residue of the chloroform extract, according to Kupchan's work, comprised about 3% by weight of the initial ethanolic extract. This 3% fraction comprises the substantial part of the anti-leukemic activity and of the maytansine. As will be seen from a study of the Kupchan patent, the procedures set forth therein, while operative on a milligram scale, for the provision of analytically pure maytansine, are not deemed practical for the provision of a sufficient amount of maytansine to make said material commercially available.

It was, therefore, deemed desirable to provide a route for the efficient and practical provision of maytansine from the aforementioned chloroform extract designated fraction V in the Kupchan patent.

SUMMARY OF THE INVENTION

It has been found that maytansine may be isolated, free from other maytansinoids, from the Kupchan chloroform fraction V in two simple sequential chromatographic steps. In the first step, the extract is charged to a silica gel column in a low polarity solvent, suitably methylene chloride, and the column eluted first with methylene chloride and subsequently with methylene chloride containing from 1% through 5% of more polar oxygenated solvents. The eluate fractions from the more polar fractions are preserved, concentrated and rechromatographed on a similar column, and eluted with a lower alkyl alkanoate, suitably with ethyl acetate. The eluate is collected and concentrated to yield substantially pure maytansine.

DESCRIPTION OF THE PREFERRED EMBODIMENTS

The starting material for the preparation of maytansine by the procedures of the present invention is maytansine containing plant material, suitably woody material. Preferred as sources are wood from *Maytenus ovatus* and *Putterlickia verrucosa*, especially preferred is *Maytenus buchananii*. This wood is ground on a hammer mill to give slivers of a size of the order of 1 cm $\times$ 1 mm, but also includes larger slivers and dust particles. The wood chips are processed in batches of approximately 1,400 Kg of wood and are extracted with ethanol suitably containing up to about 5% by weight of moisture. There are utilized approximately 5,500 to 6,500 liters of extracting solvent per 1,400 Kg batch. Extraction is carried out in a recycling, large scale Soxhlet type plant over a time of approximately 100 hours. The solvent is removed from the extract to yield an initial crude (corresponding to Kupchan fraction P of the order of 20 to 30 grams of extract per kilogram of wood charged.

The ethanolic extract (Kupchan fraction P) is then mixed with ethyl acetate and water. There is utilized ethyl acetate/water ratio of between 3:2 to 2:1. In the preferred procedures, the fraction P is initially extracted under agitation for a period of between 5 to about 10 hours using a solvent mixture having a water content at the higher end of the range and then re-extracted with additional washes having a water content at the lower end of the range. Suitably, there are employed between about 400 and about 600 liters of solvent per 100 Kg charge of fraction P in the initial wash, and between 150 and 250 liters of solvent mixture per 100 Kg of extract charged in the subsequent washes. The ethyl acetate extracts are separated, filtered, and preserved for the next step. The ethyl acetate layers, after filtration, are washed with dilute alkali. It is preferred to utilize dilute aqueous sodium hydroxide, preferably 5% sodium hydroxide. There is, preferably, utilized an initial wash of 25 to 35, preferably about 30, liters of aqueous alkali per 100 liters of ethyl acetate followed by, suitably, up to four additional washes with the same solvent having the same total wash volume — that is to say, a total wash volume of between 50 and 70, suitably about 60, liters of alkali per 100 liters of ethyl acetate.

In the preferred procedure, the alkali washes, prior to being discarded, are re-extracted with ethyl acetate which is then added to the main batch of ethyl acetate.

The ethyl acetate layers are then extracted with dilute mineral acid. It is preferred to utilize dilute hydrochloric acid, suitably 2N hydrochloric acid, in a ratio of between 3 to 7, preferably about 5, liters of aqueous acid per 100 liters of ethyl acetate extract. It is preferred to carry out between 2 and 5 acid extractions at this ratio per batch.

In the preferred procedure, it is desirable to neutralize any acid which may remain in the ethyl acetate layer. This may be done by washing the ethyl acetate with any suitable buffer which will raise the pH above, say, 6.0. It has been found that this may be readily achieved by washing with aqueous sodium acetate. There is utilized between 100 and 120 liters of sodium acetate per 100 liters of ethyl acetate at a concentration of between 3% and 5% by weight of sodium acetate in water.

The ethyl acetate extracts are then taken to dryness under reduced pressure. It is preferred to carry out this solvent stripping at as low a temperature as possible, preferably at a temperature less than 60° C., most suitably at approximately 40° C. Stripping of the solvents yields a fraction corresponding to Kupchan fraction S. This fraction constitutes approximately 20% by weight of initial crude extract corresponding to Kupchan extract P.

The foregoing ethyl acetate residue is then acylated. The acylating agent, or the procedures utilized for the acylation, are by no means critical. The acyl group employed may be alkanoyl, suitably lower alkanoyl of 1 to 5 carbon atoms, cycloalkanoyl, suitably cyclo lower alkanoyl, aroyl or arylalkanoyl, suitably phenyl lower alkanoyl, or the like. For reasons of convenience and cost, however, it has been found suitable to employ an acetylating agent as the acylating agent, and the most suitable procedure to be acetylation with acetic anydride in the presence of pyridine.

In this procedure, the pyridine is added to the ethyl acetate extract residue followed by the acetic anydride. It is preferred that the reaction be carried out at ambient temperature, utilizing between 1.1 to 1.4 Kg of pyridine and of acetic anhydride per Kg of ethyl acetate extract residue. The reaction can be considered complete in between 15 and 20 hours; however, continuing the reaction for a longer time even up to 90 hours has no deleterious effect.

Upon completion of the reaction, the solvent is removed under reduced pressure. Again, it is desirable to keep the heat input as low as possible, suitably below 60° C., most preferably at around 40° C.

In order to remove the last traces of pyridine solvent, petroleum ether, suitably heptane, is added in the stripping process, the end point of which being determined by the absence of a detectable pyridine odor.

The crude acetylated material is then partitioned between methanol, suitable 20% aqueous methanol, and carbon tetrachloride. In this procedure, carbon tetrachloride was added to the acetylated material until the material was dissolved, the 20% aqueous methanol added thereto, and after agitating and settling, the lower carbon tetrachloride layer removed. In the preferred procedure, there is utilized between 300 and 400 liters each of aqueous methanol and carbon tetrachloride per 100 Kg of acetylated residue.

In order to maximize the yields, the aforementioned aqueous methanol layers are re-extracted, suitably up to four times, with further batches of carbon tetrachloride in the ratio of 40 liters of carbon tetrachloride per 100 liters of aqueous methanol (in total). In order to further raise yield, the carbon tetrachloride washes are, themselves, re-extracted several times with 20% aqueous methanol utilizing a total of approximately 1 liter of aqueous methanol per 4 liters of carbon tetrachloride. The aqueous methanol extracts are then combined and the water content raised to 35%.

The aqueous methanol solution is extracted suitably once with 25 liters of chloroform per 100 liters of aqueous methanol, and subsequently up to four times with 10 liters of chloroform per 100 liters of methanol. The chloroform extracts are combined and the solvent stripped under reduced pressure. The stripping temperature at this stage is preferably held below 40° C. There is, thus, provided a fraction corresponding to Kupchan fraction V constituting approximately 1.5% by weight of the initial ethanolic extract corresponding to Kupchan extract P.

Chromatographic Isolation of Maytansine

The residue from the chlorofrom extraction is taken up in a solvent of low eluting strength and chromatographed on silica gel. It has been found that methylene chloride is a suitable dissolving solvent.

The chromatography is, desirably, carried out on a silica gel column. This column comprises silica gel of mesh size between 100 and 1,000 mesh, most suitably a silica gel having a mesh range between 230 and 400 mesh. There is a fairly substantial leeway in the loading ratio. There may be utilized from between as much as 20 to as little 2 parts by weight of silica gel per part by weight of chloroform extract residue charged. It has been found, however, that the best results are obtained utilizing a ratio of between 3 and 7 parts by weight of silica gel per part by weight of extract charged. In the preferred embodiments of the process, the chromatography is carried out under pressure, suitably a pressure of the order of 3.5 to 7, suitably about 5, Kg/sq. cm. which, under the conditions of the especially preferred silica gel mesh size, yields a flow rate of the order of 35 to 45 liters of solvent per hour.

Washing with methylene chloride will not elute maytansine itself. This desired fraction is eluted by utilizing a solvent mixture consisting of methylene chloride containing a more polar solvent, suitably a solvent selected from the group consisting of lower alkanols such as methanol, ethanol, propanol, isopropanol, butanol, or the like, lower alkyl ketones such as acetone, methylethyl ketone, or the like, or lower alkyl lower alkanoates such as methyl acetate, ethyl acetate, propyl acetate, butyl acetate, methyl propionate, ethyl propionate, butyl propionate, and the like, wherein in the foregoing generic terms the prefix lower alk signifies 1 to 5 carbon atoms. It is especially preferred to utilize between 1% and 10% of the lower polar solvent relative to the methylene chloride. It has been found, however, that better results are obtained by utilizing between 1% and 5% of the stronger solvent. Of the foregoing solvents, it has been found that especially favorable results are obtained by utilizing isopropyl alcohol as the more powerful solvent.

The fractions eluted with between 1% to 5%, most suitably between 3% and 4%, isopropyl alcohol in methylene chloride contain principally maytansine together with small amounts of impurities. The maytansine containing fractions constitute approximately 20% by weight of the chloroform extract residue charged.

The maytansine fractions obtained from the foregoing chromatography are concentrated and taken up once more in methylene chloride. The aforesaid fraction is then chromatographed on a silica gel column similar to that employed for the above described first stage chromatography. The column employed, and the mesh size of silica gel, is of the same order of magnitude. The charge ratio may, preferably, fall in the range of between 4 and 15 parts by weight of silica gel per part by weight of residue charged (obtained from immediately previous chromatography stage). The column is then eluted with ethyl acetate under similar pressure conditions to those set forth in the first stage. It will be understood by those skilled in the art that the exact location of the maytansine band to be eluted will vary in accordance with the exact mesh size utilized and the load ratio of the column. Nevertheless, it has been found that the principal maytansine fraction, when obtained from sources as set forth hereinabove, will be eluted after the elution of two separately noted bands of colored impurities. In a column having a load factor of 6–10 parts by weight of silica gel per part by weight of first stage chromatographic residue, maytansine begins to be eluted in 3–4 column volumes with the major portion, constituting approximately 70% by weight of the charge, as maytansine, appears in the 4.5 to 6 column volume. Removal of the solvent and crystallizing out of methylene chloride and ether yields crystalline maytansine.

It will be understood by those skilled in the art of natural product extraction that there are variations in product content from batch to batch of the source material. It will also be understood that lab scale yields may apparently bear little relationship to pilot plant yields where time factors and different methods of operation must be taken into account. Further, in the pilot scale runs, set forth hereinbelow, only the prime high maytansine containing fractions were considered. The remaining fractions containing maytansine together with maytansinoids and other contaminants were not discarded but recycled in combined residue chromatography. This combined residue chromatography utilizes the same two stage chromatography employed for isolating the prime maytansine fraction. Viewed in this context, the Kupchan procedures, run on a lab scale only, yielded about 750 mg of maytansine per Kg of extract V while the procedures of the present invention yield 1.5 to 2.0 g of maytansine per Kg of extract V in a procedure which can be carried out on a large scale.

EXPERIMENTAL

Preparation of Starting Material

*Maytenus buchananii* wood was ground into small chips of the order of 1 cm long × 1 m thick. Batches of approximately 1,400 Kg each of wood chips were subjected to pilot plant scale Soxhlet type extraction with 95% ethanol to yield, upon stripping of the solvent, approximately 45-55 Kg of concentrate per batch. This concentrate corresponds substantially to fraction P of Kupchan et al., U.S. Pat. No. 3,896,111. The aforementioned concentrate was then treated, on a pilot plant scale, essentially in accordance with the procedures set forth in Example III of Kupchan U.S. Pat. No. 3,896,111 to yield a chloroform soluble fraction corresponding substantially to fraction V of Kupchan et al., U.S. Pat. No. 3,896,111. From 106 Kg of concentrate, there is obtained, as a result of the Kupchan purification step, 1,758 g of chloroform soluble concentrate.

In other runs, 68 Kg of ethanol extract concentrate yields 548 g of chloroform soluble concentrate, and 131 Kg of ethanol extract concentrate yielded 2,262 g of chloroform soluble concentrate. This concentrate is considered to be the starting material for the purification procedures set forth hereinbelow.

In accordance with the above procedures, but in place of *Maytenus buchananii*, there may also be used wood from *Maytenus ovatus* or *Putterlickia verrucosa* to obtain an extract of substantially the same composition.

Equipment Utilized

The liquid chromatograph utilized in the present procedures comprises a pipe suitably a stainless steel pipe, provided with pressure flanges at each end thereof. There is provided a solvent tank connected through a bottom outlet to a metering pump. The solvent tank is also provided with a vent. The metering pump is connected to the top flange of the column to which is also connected a pressure release valve, the other end of which runs back to storage tank. Between the bottom flange and the column is provided a stainless steel frit to act as packing support. An outlet tube connects bottom flange to the collecting jugs. Suitably, this tube is also stainless steel.

In the equipment as set up in the pilot scale chromatographic experiments set forth hereinbelow, the storage tank 10 is a 370 liter stainless steel tank equipped with an agitator. The metering pump is a Milroyal Model C metering pump with a variable flow control from 20 to 200 liters per hour. The column itself is a 10 cm diameter by 245 cm length of stainless steel pipe wherein flanges are rated ASA 150 PSI (10 Kg/cm$^2$).

The column is prepared for use by filling it approximately half full with the solvent to be utilized. The chromatographic medium (230 to 400 mesh silica gel 60) is sprinkled into the column and allowed to settle through the liquid. The column is then packed by pumping pure solvent through the silica gel at ca. 100 psig (6.6 Kg/sq. cm.). The pressure is then released, the top flange removed, the charge placed on top of the silica gel bed, and the apparatus reassembled.

First Stage Chromatography of Chloroform Soluble Maytansine Concentrate (a) Lab scale Chromatography was carried out in accordance with the above general procedures utilizing a column 2.5 cm diameter × 100 cm long packed with 200 g of 230 to 400 mesh silica gel 60 (E. Merck and Co.) in methylene chloride.

Chloroform soluble concentrate (15.5 g) was taken up in methylene chloride (15 ml) and charged to the column. The column was eluted with methylene chloride (500 ml) and then with 4% isopropyl alcohol in methylene chloride (4000 ml). The progress of the chromatography was followed with high pressure liquid chromatography utilizing a PXS-10/25 silica gel column with 7% isopropyl alcohol/methylene chloride as the mobile phase and uv detector at 254 nm.

The maytansine containing fractions were combined and dried under reduced pressure (bath temperature 40° C.) to yield a residue which, upon crystallization (methylene chloride/ethyl ether) yielded substantially pure maytansine (2.1089 g, mp. 195°–196° C.; $C_{34}H_{46}ClN_3O_{10}$; calc. C 58.99, H 6.70, N 6.07, Cl 5.12%; found: C 58.73, H 6.88, N 5.95, Cl 4.95%; uv max. (EtOH) 233 ($\epsilon$26,200, lit; 29800) 244 sh ($\epsilon$24,300, lit. 27,100) 254 ($\epsilon$25,200, lit: 27,200) 283 ($\epsilon$4112), lit: 5,690) 290 ($\epsilon$4,000), lit: 5520) $[\alpha]_D^{25} = -122°$ (C = 0.0476, CHCl$_3$) nmr and ir as per literature. HPLC analysis: ODS column, 263 nm, ethyl acetate solvent indicates presence of minor impurity peak.

(b) Pilot Plant scale

Chromatography was carried out in accordance with the above general procedures utilizing a column 10 cm diameter × 245 cm long packed with 10 Kg of 230 to 240 mesh silica gel (E. Merck and Co.) in methylene chloride.

Chloroform soluble concentrate (1,900 g) was taken up in methylene chloride and charged to the column. The column was eluted with 3% isopropyl alcohol/methylene chloride ( 120l/Fracs. 1–6) and then with 5% isopropyl alcohol in methylene chloride ( 500 l/Fracs. 7–30). The progress of the chromatography was followed with high pressure liquid chromatography utilizing a PXS-10/25 silica gel column with 7% isopropyl alcohol/methylene chloride as the mobile phase and uv detector at 254 nm.

The principal maytansine containing fractions 16–22 were combined and dried under reduced pressure (bath temperature 40° C.) to yield a residue of substantially pure maytansine (28.4 g).

Complete Chromatographic Purification of Maytansine (a) Lab scale

The maytansine product (2.1089 g) obtained in the foregoing example part (a) was rechromatographed on a column similar to that utilized in the foregoing example. Fractions of eluate are collected in 10 ml (0.05 column volume) batches. Fractions 175 through 236 yield, upon evaporation to dryness, pure maytansine (single peak on HPLC and TLC). Recrystallization (methylene chloride/ether) yields maytansine 1.262 g (m.p. 190°–191° C; $C_{34}H_{46}ClN_3O_{10}$; calc. C 58.99, H 6.70, N 6.07, Cl 5.12%; found: C 58.73, H 6.88, N 5.95, Cl 4.95%; uv max. (EtOH) 232 ($\epsilon$28,137) 243 sh ($\epsilon$25,760) 254 ($\epsilon$26,200) 282 ($\epsilon$5,317) 290 ($\epsilon$5,284) $[\alpha]_D^{25}$ = −143° (C = 0.197, $CHCl_3$).

(b) Pilot Plant scale

The maytansine product (28.4 g) obtained in the foregoing example, part (b), was rechromatographed on a column similar to that utilized in the foregoing example, part (a). Fractions of eluate are collected in 10 ml (0.05 column volume) batches. Fractions 175 through 236 yield, upon evaporation to dryness, pure maytansine (single peak on HPLC and TLC). Fractions 96–170 contain maytansine of sufficient purity to combine with the principal fractions. Recrystallization (methylene chloride/ether) yields 1.8997 g (m.p. 190°–191° C.).

We claim:

1. In a method of isolating maytansine, from woody material containing same, which comprises, using as starting material, an extract from the aforesaid sources which is soluble in 95% aqueous ethanol and ethyl acetate and insoluble in 5% aqueous sodium hydroxide and in 2N aqueous hydrohloric acid, acylating said material and isolating the fraction thereof which is soluble in 20%–35% aqueous methanol and in chloroform, but insoluble in carbon tetrachloride, the steps which comprise subjecting said fraction to
   (a) chromatography on silica gel of mesh 100 to 1,000 in methylene chloride,
   (b) eluting with methylene chloride followed by a more polar solvent consisting of methylene chloride containing 1%–10% by volume of a member selected from the group consisting of lower alkanols, lower alkyl ketones, and lower alkyl lower alkanoids wherein the lower alk group contains 1–5 carbon atoms,
   (c) preserving the eluate fractions from said more polar solvent and removing said solvent therefrom to provide a residue of substantially pure maytansine.

2. A process of claim 1 wherein the woody material is derived from *Maytenus ovatus*, *Maytenus buchananii* or *Putterlickia verrucosa*.

3. A process according to claim 1 wherein there are utilized:
   in step (a) between 3 and 7 parts by weight of silica gel of mesh size 230 to 400 per part by weight of extract charged and
   in step (b) as a more polar solvent 2–5% by weight of isopropyl alcohol in methylene chloride.

4. A process according to claim 1 wherein the acylation is acetylation in pyridine.

5. A process according to claim 1 comprising the initial steps (a), (b) and (c) and additionally comprising the steps of
   (d) rechromatographing said residue of substantially pure maytansine on silica gel of mesh 100 to 1,000 in methylene chloride and eluting with ethyl acetate,
   (e) collecting the eluate and removing the solvent therefrom to yield pure maytansine.

6. A process according to claim 5 wherein there are utilized:
   in initial step (a) between 3 and 7 parts by weight of silica gel mesh size 230 to 400 per part by weight of extract charged,
   in initial step (b) as a more polar solvent, 2%–5% by weight of isopropyl alcohol in methylene chloride,
   in step (d) between 4 and 15 parts by weight of silica gel of mesh size 230 to 400 per part by weight of step (c) residue charged.

7. A process according to claim 5 wherein the acylation is acetylation in pyridine.

* * * * *